US00PP11761P2

(12) United States Plant Patent
Bergman

(10) Patent No.: US PP11,761 P2
(45) Date of Patent: Jan. 30, 2001

(54) HIBISCUS PLANT NAMED 'COCONUT WIND'

(75) Inventor: Wendy R. Bergman, Lehigh Acres, FL (US)

(73) Assignee: Yoder Brothers, Inc., Barberton, OH (US)

( * ) Notice: Under 35 U.S.C. 154(b), the term of this patent shall be extended for 0 days.

(21) Appl. No.: 09/333,128

(22) Filed: Jun. 14, 1999

(51) Int. Cl.[7] ..... A01H 5/00
(52) U.S. Cl. ..... Plt./257
(58) Field of Search ..... Plt./257

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Hibiscus plant named 'Coconut Wind', characterized by its very glossy, undulate, very dark green leaves; upright, compact, outwardly spreading, uniform, dense and symmetrical plant habit that is appropriate for container production; very freely flowering; numerous white-colored flowers with dark red "eyes"; short peduncles; good resistance to flower bud abscission; relatively resistant to pathogens common to Hibiscus grown under Florida production conditions; and excellent postproduction longevity.

2 Drawing Sheets

BACKGROUND OF THE INVENTION

The present invention relates to a new and distinct cultivar of Hibiscus, botanically known as *Hibiscus rosa-sinensis*, and hereinafter referred to by the cultivar name Coconut Wind.

The new Hibiscus is a product of a planned breeding program conducted by the Inventor in Alva, Fla. The objective of the breeding program is to create new freely-branching Hibiscus cultivars with uniform and compact plant habit appropriate for container production, early and uniform flowering, numerous flowers per lateral branch, desirable flower color, resistance to flower bud abscission, and good postproduction longevity.

The new Hibiscus originated from a cross made by the Inventor in Alva, Fla., of a proprietary *Hibiscus rosa-sinensis* selection, designated as code No. YB-1242, as the female, or seed, parent with the *Hibiscus rosa-sinensis* cultivar Light Wind, disclosed in U.S. Plant Pat. No. 10,593, as the male, or pollen, parent. The cultivar Coconut Wind was discovered and selected by the Inventor as a flowering plant within the progeny of the stated cross in a controlled environment in Alva, Fla., on Sep. 15, 1995.

Compared to plants of the female parent, the proprietary Hibiscus selection code No. YB-1242, plants of the new Hibiscus are more upright; have smaller and darker green foliage; flower about 5 to 7 days earlier; and are less attractive to whiteflies. Plants of new Hibiscus flower about 2 to 3 days later; are less susceptible to diseases common to Hibiscus grown under Florida production conditions; and differ in flower color compared to plants of the male parent, the cultivar Light Wind.

Plants of the new Hibiscus are distinguished from its sibling, the cultivar Golden Wind, U.S. Plant patent application Ser. No. 09/333,126 submitted concurrently with this application, in flower color.

Asexual reproduction of the new Hibiscus by terminal cuttings taken in a controlled environment in Alva, Fla., has shown that the unique features of this new Hibiscus are stable and reproduced true to type in successive generations.

SUMMARY OF THE INVENTION

The cultivar Coconut Wind has not been observed under all possible environmental conditions. The phenotype may vary somewhat with variations in environment such as temperature, light intensity, nutrition and water status without, however, any variance in genotype.

The following traits have been repeatedly observed and are determined to be the unique characteristics of 'Coconut Wind'. Theee characteristics in combination distinguish 'Coconut Wind' as a new and distinct cultivar:

1. Very glossy, undulate, very dark green leaves.
2. Upright, compact, outwardly spreading, uniform, dense and symmetrical plant habit that is appropriate for container production.
3. Very freely flowering, numerous white-colored flowers with dark red "eyes" and short peduncles.
4. Good resistance to flower bud abscission.
5. Relatively resistant to pathogens common to Hibiscus grown under Florida production conditions.
6. Excellent postproduction longevity.

Plants of the new Hibiscus can be compared to plants of the cultivar White Cloud, not patented. However, in side-by-side comparisons conducted in Alva, Fla., plants of the new Hibiscus differ from plants of the cultivar White Cloud in the following characteristics:

1. Plants of the new Hibiscus are more upright than plants of the cultivar White Cloud.
2. Plants of the new Hibiscus have smaller leaves than plants of the cultivar White Cloud.
3. Flowers of plants of the new Hibiscus are slightly smaller than flowers of plants of the cultivar White Cloud.
4. Plants of the new Hibiscus are less susceptible to diseases common to Hibiscus grown under Florida production conditions than plants of the cultivar White Cloud.

BRIEF DESCRIPTION OF THE PHOTOGRAPHS

The accompanying colored photographs illustrate the overall appearance of the new Hibiscus, showing the colors as true as it is reasonably possible to obtain in colored reproductions of this type.

The photograph on the first sheet comprises a side perspective view of a typical plant of 'Coconut Wind'.

The photograph on the second sheet comprises a close-up view of a typical flower of 'Coconut Wind'. Both photographs were taken when plants were about 7 months old. Flower and foliage colors in the photographs may appear different from the actual colors due to light reflectance.

DETAILED BOTANICAL DESCRIPTION

The following observations, measurements and values describe plants grown in Alva, Fla., with five plants per 16.5-cm containers in polyethylene-covered greenhouses, during the late spring under conditions which closely approximate commercial production. Night temperatures ranged between 13 to 24 degrees centigrade. Day temperatures ranged between 21 and 32 degrees centigrade. Plants were about 7 months old when descriptions were taken. In the description, color references are made to The Royal Horticultural Society Colour Chart except where general terms of ordinary dictionary significance are used.

Botanical classification: *Hibiscus rosa-sinensis* cultivar Coconut Wind.

Parentage:

*Female or seed parent.*—*Hibiscus rosa-sinensis* proprietary selection designated as code No. YB-1242.

*Male or pollen parent.*—*Hibiscus rosa-sinensis* cultivar Light Wind, disclosed in U.S. Plant Pat. No. 10,593.

Propagation:

*Type.*—By terminal cuttings.

*Time to initiate roots.*—About 10 days at temperatures of 24° C.

*Time to develop roots.*—About 28 days at temperatures of 24° C.

*Rooting habit.*—Moderately vigorous, thick and well-branched.

Plant description:

*Plant form and growth habit.*—Perennial, evergreen, upright, outwardly spreading, compact, uniform, dense and symmetrical plant habit.

*Branching habit.*—Freely branching, usually about four lateral branches develop after removal of terminal apex.

*Plant height, soil level to top of flowers.*—About 31 cm.

*Plant diameter, area of spread.*—About 46 cm.

*Lateral branch description.*—Length: About 23 cm. Diameter: About 5.5 mm. Texture: Immature, smooth; mature, woody and rough. Color: Immature: Greener than 147A. Mature: Gray, close to 197A to 197B.

Foliage description:

*Arrangement.*—Alternate, single; numerous; symmetrical.

*Length.*—About 8.1 cm.

*Width.*—About 7.1 cm.

*Shape.*—Ovate.

*Apex.*—Narrowly acute.

*Base.*—Obtuse to slightly cordate.

*Margin.*—Serrate.

*Aspect.*—Undulate.

*Texture.*—Glabrous and glossy on both surfaces.

*Color.*—Young foliage, upper surface: Darker and greener than 146A. Young foliage, lower surface: Close to 146A. Mature foliage, upper surface: Much darker than 147A. Mature foliage, lower surface: Greener than 147A.

*Petiole.*—Length: About 2.1 cm. Diameter: About 2.75 mm. Texture: Mostly smooth with very fine pubescence on upper surface. Color: A combination of 144A and 146A with brownish overtones.

Flower description:

*Natural flowering season.*—Usually spring and summer or during periods of warm weather.

*Flower arrangement.*—Flowers arranged singly at terminal leaf axils. Very freely flowering with usually about three or four flower buds and/or open flowers per terminal apex. Flowers face upright and slightly outward.

*Flower appearance.*—Rounded, white-colored petals with dark red "eye". Flowers are open for about one day before closing. Flowers persistent.

*Flower diameter.*—About 12.5 cm.

*Flower bud (just before showing color).*—Rate of opening: About one or two days depending on temperatures. Length: About 2.9 cm. Diameter: About 1.3 cm. Shape: Elliptic.

*Petals.*—Texture: Smooth, satiny. Arrangement: Corolla consists of five petals that overlap. Shape: Spatulate with rounded apex. Margin: Entire, but slightly ruffled. Length: About 8.2 cm. Width: About 6.1 cm. Color: Upper surface: White, 155D; towards margin, close to 11D. Lower surface: White; towards margin, close to 11C to 11D. Throat or "eye": Dark red, 53A; glossy.

*Sepals.*—Appearance: Five sepals fused into a star-shaped calyx. Shape: Linear. Texture: Slightly pubescent. Color, outer surface: Darker than 146A.

*Bracts.*—Appearance: About six fused at base. Length: About 1.5 cm. Width: About 3 mm. Shape: Linear. Color: 147A.

*Peduncles.*—Length: Short, about 3.2 cm. Diameter: About 2 mm at base. Angle: Upright to slightly bent. Strength: Strong, flexible. Texture: Slightly pubescent. Color: Greener than 146A.

*Reproductive organs.*—Androecium: Stamen number: Numerous, about 35. Stamen length: About 5 mm. Filament color: 52B. Anther size: About 1 mm by 0.5 mm. Amount of pollen: Abundant. Pollen color: 14A. Gynoecium: Pistil length: About 9.5 cm. Style color: Base, dark red, 46A; mid-section and apex, white, 155D. Stigma appearance: Five, rounded. Stigma diameter: About 2 mm. Stigma color: Close to 14A.

Disease resistance: Plants of the new Hibiscus grown under Florida production conditions have shown to be relatively resistant to pathogens common to Hibiscus.

Seed production: Seed production has not been observed.

It is claimed:

1. A new and distinct Hibiscus plant named 'Coconut Wind', as illustrated and described.

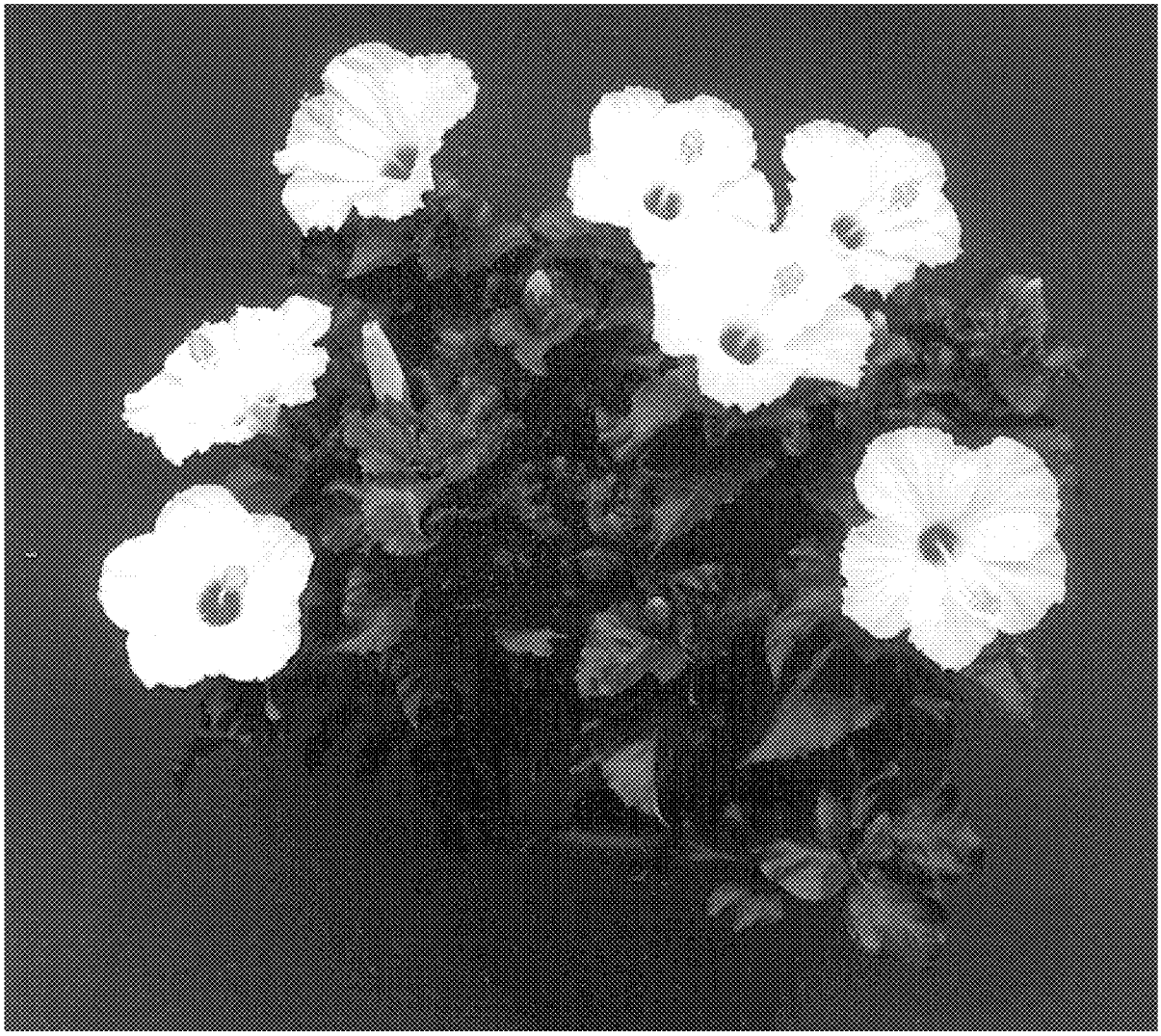

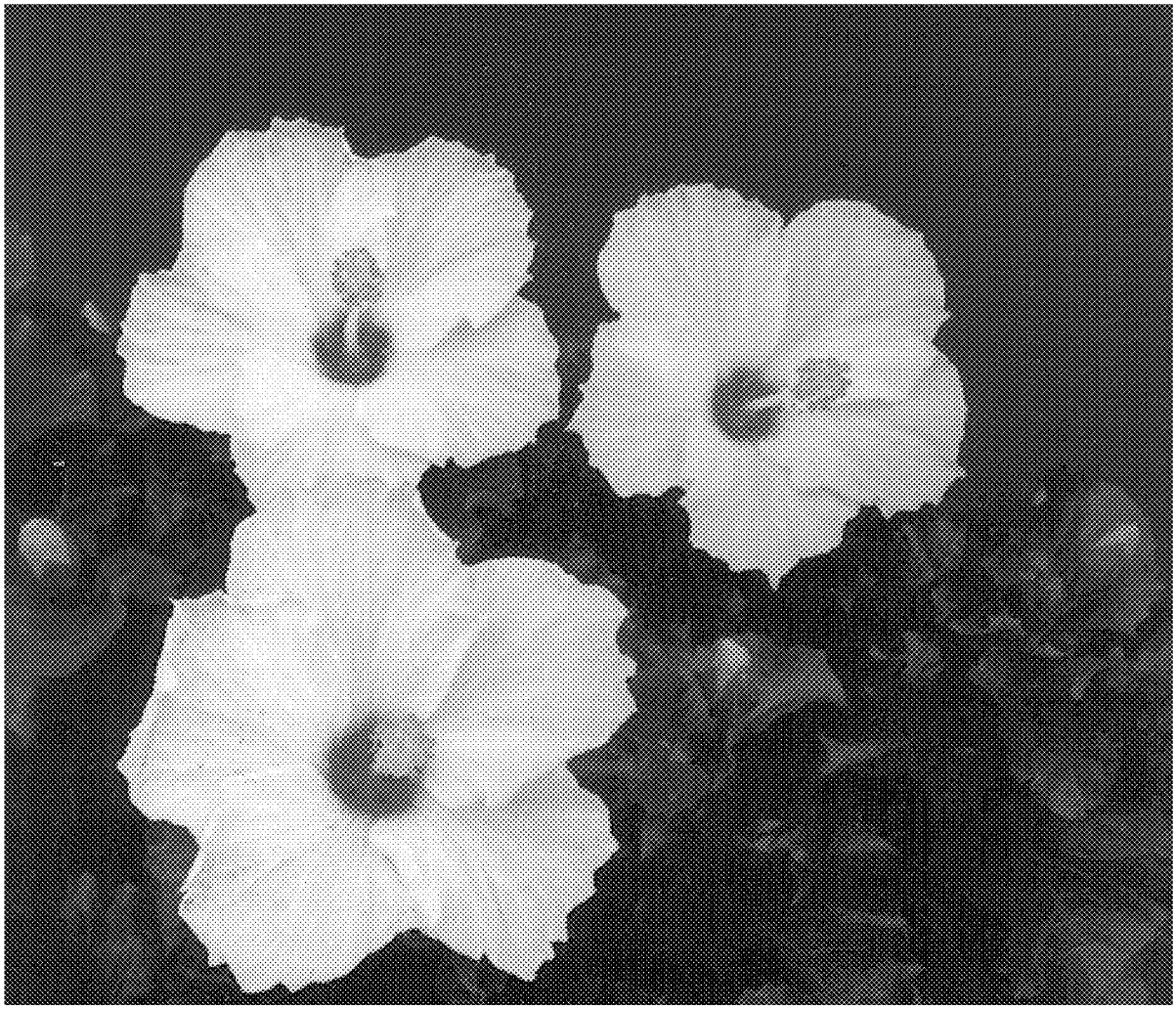

* * * * *